United States Patent [19]
Tanaka et al.

[11] Patent Number: 5,162,234
[45] Date of Patent: Nov. 10, 1992

[54] AUTOMATIC BLOOD CELL PARTICLE PATTERN JUDGING METHOD

[75] Inventors: Satoshi Tanaka, Hino; Haruhisa Watanabe; Shinya Matsuyama, both of Hachioji, all of Japan

[73] Assignee: Olympus Optical Co., Ltd., Tokyo, Japan

[21] Appl. No.: 623,063

[22] Filed: Dec. 6, 1990

[30] Foreign Application Priority Data

Dec. 11, 1989 [JP] Japan ................. 1-318949

[51] Int. Cl.⁵ .......................................... G01N 21/17
[52] U.S. Cl. .............................. 436/165; 436/164; 436/518; 436/805; 422/73; 356/39; 356/434; 356/441; 382/6
[58] Field of Search ............... 436/34, 63, 69, 164, 436/518, 805, 165; 422/73; 356/39, 434, 441; 382/6; 364/413.01; 73/64.1

[56] References Cited

U.S. PATENT DOCUMENTS 4,575,492  3/1986  David ......................... 436/164
4,727,033  2/1988  Hijikata ........................ 436/69

FOREIGN PATENT DOCUMENTS 58-105065  9/1983  Japan .
61-215948  9/1986  Japan .
8907255  8/1989  PCT Int'l Appl. .

*Primary Examiner*—James C. Housel
*Assistant Examiner*—David Redding
*Attorney, Agent, or Firm*—Stevens, Davis, Miller & Mosher

[57] ABSTRACT

Automatic particle pattern judging method, in which particles to be tested, such as blood cell particles, are delivered into not only a reaction vessel but also a reference vessel, and an amount of the particles delivered into the reference vessel is measured and a judgement whether the particle pattern formed in the reaction vessel is agglutinated or not is conducted by correcting values of a reaction liquid contained in the reaction vessel concerning parameters for the judgement or correcting threshold values, with which the values of the test liquid concerning the parameters should be compared in accordance with the amount of the particles delivered into the reference vessel. Therefore, by the method according to the invention, even when the amount of particles to be tested delivered into the reaction vessel is varied for some reason, it is possible to judge correctly whether the particle pattern is agglutinated or not.

11 Claims, 1 Drawing Sheet

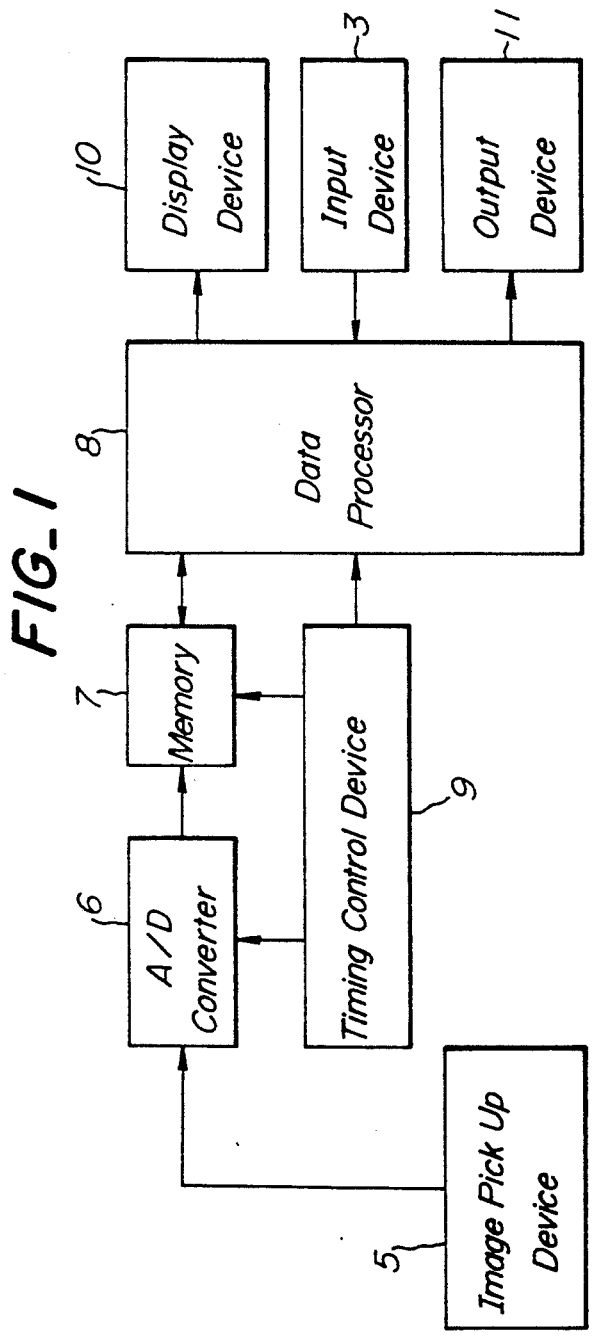
FIG._1
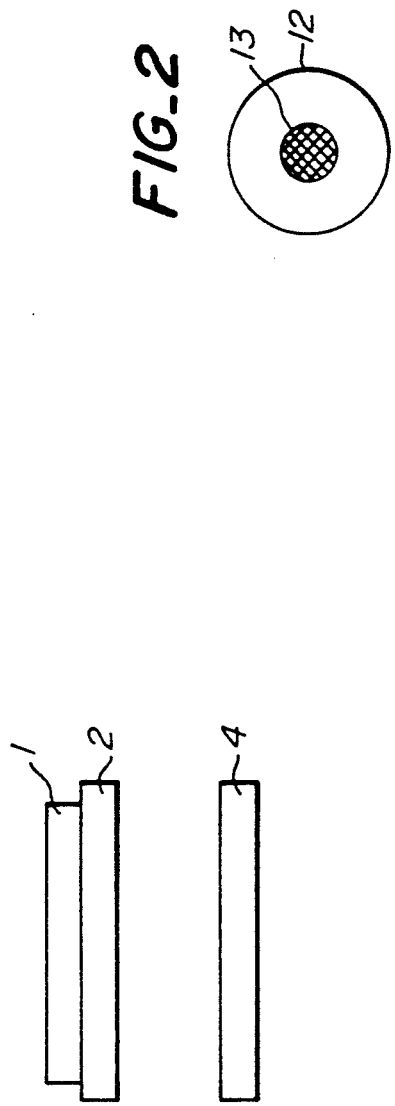
FIG._2

AUTOMATIC BLOOD CELL PARTICLE PATTERN JUDGING METHOD

BACKGROUND OF THE INVENTION a) Field of the Invention

The present invention relates to an automatic particle pattern judging method, which is for judging particle patterns formed in bottom surfaces of reaction vessels by an immunological agglutination reaction. Such judgement is conducted for a clinical test purpose. In the method according to the invention, the particle patterns are measured in an optical manner and then it is automatically judged whether the particle patterns are agglutinated or not.

b) Prior Art Statement

An immunological agglutination reaction is used for judging a type of composition of blood, such as erythrocyte type and leukocyte type, for analyzing a shape or a kind of platelet or lymphocyte and for detecting a presence of antibody, antigen, specific protein and/or virus in a sample liquid, such as blood, humor and urea. The immunological agglutination analysis is conducted such that the sample is mixed with reagent such as hemocyte particles, rates particles and carbon particles to introduce an agglutination reaction; and the particle pattern formed in the reaction vessel by the agglutination reaction is measured to judge whether the pattern is agglutinated or not. It is possible to judge visually whether the particle pattern is agglutinated or not, but there are some problems in objectivity and in measuring accuracy. Therefore, an automatic particle pattern judging method is widely used. By the method, it is possible to judge the particle pattern automatically with a high detecting accuracy and thus a lot of specimens can be processed.

Such automatic particle pattern judging method is suggested, for instance, in Japanese Preliminarily Laid Open Patent Publication No. 58-105065, in which the judgement of the particle pattern is conducted by using a parameter of a ratio between a light intensity of a center portion of the particle pattern to be tested and that of a peripheral portion thereof; and it is also suggested in Japanese Preliminarily Laid Open Patent Publication No. 61-215948, in which the judgement is conducted such that an area of a portion where the particles are gathered to form an agglutination pattern or a non-agglutination pattern is obtained by using an image picking up device and then whether the particle pattern is agglutinated or not is judged by comparing the area with a given threshold value.

In such automatic particle pattern judging method, however, there is a problem that blood cell particles to be tested sometimes could not be delivered exactly into the reaction vessel in accordance with a given amount. The following are considered as causes of such mis-delivery: sexual difference or age difference in patients; a condition of centrifugal separation, which is conducted for separating the sample into plasma and blood cell; a variation of sample caused by a long time delay since the sample is picked up from patients; an amount or a kind of anticoagulant which has been mixed into the sample; and a buffy coat included in the sample. Under such situations, the judgement of the agglutination pattern cannot be conducted correctly. For instance, the amount of the blood cell particles to be tested delivered into the reaction vessel is so small that the particle pattern formed in the reaction vessel is sometimes judged as a negative pattern nevertheless the pattern is actually pseudopositive; or the amount of the blood cell particles to be tested is so large that the pattern is sometimes judged as a pseudonegative pattern instead of positive pattern.

Therefore, an operator who operates a particle pattern analyzing apparatus have to correct the judgement result of agglutination reaction. That is to say, the operator firstly has to guess the amount of the blood cell particles delivered in the reaction vessel and guess a proper particle pattern in accordance with the guessed amount of the blood cell particles, and then the operator corrects the judgement result of the particle pattern judged by the automatic judging apparatus. However, such correction of the judgement result is sometimes impossible: and in such a case, it is necessary to re-examine the sample blood all over again.

As stated above, according to the conventional particle pattern judging method, in case the blood cell particles to be tested cannot be delivered into the reaction vessel in an exact manner in accordance with the proper given delivering amount, the operator has to find out the mis-delivery and correct the judgement result. Accordingly, a lot of labor is necessary because the operator has to watch and confirm all of the particle patterns to be tested in a visual manner. Further to this, there is an individual difference in the operator's visual watching and confirming, and even if all of the watching and confirming is conducted by the same operator, it could not keep the judgement results constant. Furthermore, when the mis-delivery of the particles cannot be found out by the operator, there is a danger of misjudgement. The operator's guess as to the delivery amount of the particles in a visual manner has its limitation and it is difficult to exactly guess the amount of the particles delivered into the reaction vessel. Additionally, in case the operator's guess in a visual manner is impossible and the re-examination is requested, it would take a lot of labor and sometimes the re-examination could not be conducted when the amount of the particles to be tested is so small. Additionally, in a large sized analyzing apparatus, in which many specimens are processed with high speed, there is a danger that the mis-delivery of the particles cannot be found out resulting from the operator's fatigue.

It should be noted that in the particle pattern judging method with the aid of the agglutination reaction, the judgement largely depends upon a concentration of the blood cell particles, and therefore the variation of the delivery amount of the blood cell particles t be tested influences the judgement result delicately.

SUMMARY OF THE INVENTION

The automatic particle pattern judging method according to the present invention has for its object to correctly judge the particle patterns formed in the reaction vessel without being influenced by a concentration of particles to be tested which has been delivered into the reaction vessel.

In order to carry out the above object, the method according to the invention comprises the steps that:

delivering blood cell particles to be tested into a reaction vessel as well as a reference vessel;

delivering a reagent into said reaction vessel for causing an agglutinating reaction in the reaction vessel to make a reaction liquid;

delivering a dilution liquid into said reference vessel to make a reference liquid;

leaving the reaction liquid and the reference liquid for a given time in a stationary manner to form a particle pattern in the bottom surface of the reaction vessel and to collect the blood cell particles in a center portion of the reference vessel, respectively;

obtaining an amount of the blood cell particles delivered into the reference vessel by picking up an image information of the reference liquid and obtaining values of the reaction liquid concerning at least one parameter for judging whether the particle pattern formed in the reaction vessel is an agglutination pattern or a non-agglutination pattern by picking up the image information of the reaction liquid;

correcting the value of the reaction liquid concerning the parameter in accordance with the amount of the blood cell particles delivered into the reference vessel; and judging the particle pattern formed on the bottom surface of the reaction vessel in accordance with said corrected value of the test liquid concerning said parameter.

The method according to the invention has another aspect which comprises the steps of:

delivering blood cell particles to be tested into a reaction vessel as well as a reference vessel;

delivering a reagent into said reaction vessel for causing an agglutinating reaction in the reaction vessel to make a reaction liquid;

delivering a dilution liquid into said reference vessel to make a reference liquid;

leaving the reaction liquid and the reference liquid for a given time in a stationary manner to form a particle pattern on the bottom surface of the reaction vessel and to collect the blood cell particles in a center portion of the reference vessel, respectively;

obtaining an amount of the blood cell particles delivered into the reference vessel by picking up an image information of the reference liquid and obtaining values of the reaction liquid concerning at least one parameter for judging whether the particle pattern formed in the reaction vessel is an agglutination pattern or a non-agglutination pattern by picking up an image information of the reaction liquid;

correcting given threshold values, which are used for comparing the values of the test liquid concerning the parameters in accordance with the amount of the blood cell particles delivered in the reference vessel; and comparing the values of the reaction liquid concerning the parameters with the corrected threshold values and judging whether the particle pattern formed in the reaction vessel is agglutinated or not in accordance with the comparison result.

According to the method of the invention, even when the amount of the blood cell particles delivered into the reaction vessel is varied for some reason, it is possible to judge exactly whether the particle pattern formed therein is agglutinated or not.

BRIEF DESCRIPTION OF THE DRAWINGS

FIG. 1 is a block diagram showing an immunological analyzing apparatus in which the method according to the invention is conducted; and FIG. 2 is a plan view depicting a reference well in which a reference liquid is contained.

DETAILED EXPLANATION OF THE PREFERRED EMBODIMENTS

The first embodiment of the present invention will be explained in accordance with FIG. 1. In a microplate 1 there are formed a plurality of wells in a matrix manner; and each well has a conical bottom surface. One half of the wells are used as reference wells and the other half as reaction wells. Blood cell particles to be tested are delivered into the reference well and the reaction well; and the blood cell particles in the reference well are diluted by physiological saline to make a reference liquid; antiserum is delivered into the reaction well as a reagent to make a reaction liquid. The microplate 1 is put on a stand 2 and is left for several hours to cause a natural sedimentation in each well. It should be noted that an agglutinating reaction is not caused by the physiological saline in the reference well and the characteristic of the blood cell particles is not changed thereby.

Thereafter an operator gives an order to an analyzing apparatus to start a measurement of the reference liquid and the reaction liquid contained in the wells of the microplate 1 via an input device 3 of the apparatus. A light emanated from a light source 4 is transmitted through the stand 2, which is made by a transparent or a semitransparent material, and the light is made incident upon bottom surfaces of the wells of the microplate 1. In order to prevent a complex refraction of the light, it is desired to provide an upper surface of the stand 2 closer to a lower surface of the microplate 1 as well as possible. Above the stand 2, there is provided an image pick up device 5 to introduce an image information of particle pattern formed in each reaction well and an image information of the reference liquid contained in each reference well. The thus obtained image information of each well of the microplate 1 is converted to an electric signal by the image pick up device 5 and then supplied to an A/D converter 6 to be converted to a digital signal.

The digital signal representing the image information of the test liquid and reference liquid are supplied to a memory device 7. Timing when the digital signal should be supplied to the memory device 7 is controlled by a timing control device 9 and a data processor 8. The timing control device 9 is connected to the A/D converter 6, the memory device 7 and the data processor 8, respectively, to control the timings when the signals should be supplied to these devices.

In the data processor 8, the image information of the reference liquid contained in the reference well is processed to obtain relatively an amount of blood cell particles delivered into the reference well. That is to say, as depicted in FIG. 2, in the reference well of the microplate 1, the blood cell particles are gathered to the center portion of the reference well 12 and a dark portion is formed in the center portion by the natural segmentation; and the light intensity of the center portion of the well becomes darker than the peripheral portion thereof in a contrast manner. Therefore, an area of the dark portion 13 formed by the blood cell particles can be obtained by measuring a radius of the dark portion. It is possible to relatively obtain the delivery amount of blood cell particles delivered into the reference well on the basis of a result that the more the amount of blood cell particles delivered into the reference well the more the number of pixels of portions corresponding to the dark portion as well as the larger the area of the dark portion 13. It should be noted that the area of the dark portion may be obtained by differentiating the image information of the reference liquid contained in the reference well 12 to detect an edge of the dark portion 13 and then counting a number of pixels existing inside of the edge.

Next, in the data processor 8, values concerning parameters for judging whether the particle pattern formed in the reaction well is agglutinated or not is obtained by processing the image information, which is stored in the memory device 7, of the test liquid contained in the reaction well. There are suggested an area of the particle pattern formed in a bottom surface of the reaction well and/or a ratio between the light intensity of the center portion of the reaction well and that of the peripheral portion thereof as the parameters for judgement.

Next, the thus obtained values concerning the parameters for judgement are corrected in accordance with the delivery amount of the blood cell particles delivered into the reference well, which has already been obtained by processing the image information of the reference liquid in the reference well by the data processor 8. That is to say, a relation between the delivery amount of the blood cell particles in the reference well and the value concerning each parameter for the judgement is preliminarily obtained, and the relation is represented by a correction curve; and then the values concerning the parameters are corrected on the base of the correction curve. Finally, the corrected values are compared with given threshold values to automatically judge whether the particle pattern is agglutinated or not.

The thus obtained correction curve and the judgement result are displayed on the display device 10 and the judgement result is produced by an output device 11 as a data.

In the above embodiment, in order to correctly judge whether the particle patterns are agglutinated or not, the value of the test liquid concerning the parameter for judgement is corrected in accordance with the delivery amount of the blood cell particles delivered into the reference well. It is possible to judge the particle pattern formed in the reaction well by correcting the threshold value which is used for comparing the value concerning the parameter. That is to say, the test liquid and reference liquid are delivered into the reaction well and reference well formed in the microplate 1; the microplate 1 is put on the stand 2; the images of the test liquid and the reference liquid are picked up by the image pick up device 6: the image informations are processed in each device; the delivered amount of the blood cell particles delivered into the reference well is obtained by processing the image information of the reference liquid; the threshold value is corrected in accordance with the delivered amount of the blood cell particles in the reference well. As well as the first embodiment, the relation between the delivery amount of the blood cell particles and the value concerning parameters for judgement is preliminarily obtained and the relation is represented as the correction curve. Additionally, the threshold value for comparing the values concerning the parameter is corrected in accordance with the correction curve. In addition, the particle pattern formed in the reaction vessel is judged by comparing the values concerning the parameters with the corrected threshold value.

As stated above, by the method according to the invention, even when the delivery amount of the blood cell particles to be tested is varied, it is possible to correctly judge whether the particle pattern is agglutinated or not. Particularly, an attenuated positive agglutinated pattern can be exactly judged. According to the method of the invention, it is possible to decrease the mis-judgement because it becomes unnecessary that the operator has to watch and confirm all particle patterns. Further, constant judgement result can be obtained without respect to the skillness of the operator. Furthermore, the judgement result can be obtained without depending upon the centrifugal separating condition, and the difference in the particle condition caused by the amount and the kind of the anticoagulant to be mixed therein.

What is claimed is:

1. An automatic particle pattern judging method comprising the following steps:
    delivering blood cell particles to be tested into a reaction vessel as well as a reference vessel;
    delivering reagent into said reaction vessel for causing an agglutinating reaction in the reaction vessel to make a reaction liquid;
    delivering a dilution liquid into said reference vessel to make a reference liquid;
    leaving the reaction liquid and the reference liquid for a given time in a stationary manner to form a particle pattern in the bottom surface of the reaction vessel and t collect the blood cell particles in a center portion of the reference vessel, respectively;
    obtaining an amount of the blood particles delivered into the reference vessel by picking up an image information of the reference liquid and obtaining values of the reaction liquid concerning at least one parameter for judging whether the particle pattern formed in the reaction vessel is an agglutination pattern or a non-agglutination pattern by picking up an image information of the reaction liquid;
    correcting the values of the reaction liquid concerning the parameter in accordance with the amount of the blood cell particles delivered into the reference vessel; and
    judging the particle pattern formed on the bottom surface of the reaction vessel in accordance with said corrected value of the reaction liquid concerning said parameter.

2. An automatic particle pattern judging method according to claim 1, wherein:
    said parameter comprise an area of said particle pattern formed in the bottom surface of the reaction vessel.

3. An automatic particle pattern judging method according to claim 1, wherein:
    said parameter comprises a ratio between a light intensity of a center portion of the reaction vessel and that of a peripheral portion of the reaction vessel.

4. An automatic particle pattern judging method according to claim 1, wherein:
    said blood cell particles amount obtaining step comprises the steps of measuring a radius of dark portion formed by the blood cell articles gathered in a center portion of the reference vessel and counting an area of the dark portion.

5. An automatic particle pattern judging method according to claim 1, wherein:
    said blood cell particles amount obtaining step comprises the steps of differentiating the image information of the reference liquid to detect an edge of a dark portion formed by the blood cell particles gathered in a center portion of the reference vessel and counting a number of pixels existing inside of the edge.

6. An automatic particle pattern judging method comprising the steps of:

delivering blood cell particles to be tested into a reaction vessel as well as a reference vessel;

delivering a reagent into said reaction vessel for causing an agglutinating reaction in the reaction vessel to make a reaction liquid;

delivering a dilution liquid into said reference vessel to make a reference liquid;

leaving the reaction liquid and the reference liquid for a given time in a stationary manner to form a particle pattern on the bottom surface of the reaction vessel and to collect the blood cell particles in the center portion of the reference vessel, respectively;

obtaining an amount of the blood cell particles delivered into the reference vessel by picking up image information of the reference liquid and obtaining values of the reaction liquid concerning at least one parameter for judging whether the particle pattern formed in the reaction vessel is an agglutination pattern or a non-agglutination pattern by picking up an image information of the reaction liquid, said blood cell particles amount obtaining step comprising the steps of measuring a radius of dark portion formed by the blood cell particles gathered in a center portion of the reference vessel and counting an area of the dark portion;

correcting given threshold values, which are used for comparing the values of the reaction liquid concerning the parameters in accordance with the amount of the blood cell particles delivered in the reference vessel; and comparing the values of the reaction liquid concerning the parameters with the corrected threshold values and judging whether the particle pattern formed in the reaction vessel is agglutinated or not in accordance with the comparison result.

7. An automatic particle pattern judging method according to claim 6, wherein:

said parameters comprise an area of said particle pattern formed in the bottom surface of the reaction vessel.

8. An automatic particle pattern judging method according to claim 6, wherein:

said parameter comprises the ratio between the light intensity of a center portion of the reaction vessel and that of a peripheral portion of the reaction vessel.

9. An automatic particle pattern judging method comprising the steps of:

delivering blood cell particles to be tested into a reaction vessel as well as a reference vessel;

delivering a reagent into said reaction vessel for causing an agglutinating reaction in the reaction vessel to make a reaction liquid;

deliverying a dilution liquid into said reference vessel to make a reference liquid;

leaving the reaction liquid and the reference liquid for a given time in a stationary manner to form a particle pattern on the bottom surface of the reaction vessel and to collect the blood cell particles in the center portion of the reference vessel, respectively;

obtaining an amount of the blood cell particles delivered into the reference vessel by picking up image information of the reference liquid and obtaining values of the reaction liquid concerning at least one parameter for judging whether the particle pattern formed in the reaction vessel is an agglutination pattern or a non-agglutination pattern by picking up an image information of the reaction liquid, said blood cell particles amount obtaining step comprising the steps of differentiating the image information of the reference liquid to detect an edge of a dark portion formed by the blood cell particles gathered in a center portion of the reference vessel and counting the number of pixels existing inside of the edge;

correcting given threshold values, which are used for comparing the values of the reaction liquid concerning the parameters in accordance with the amount of the blood cell particles delivered in the reference vessel; and comparing the values of the reaction liquid concerning the parameters with the corrected threshold values and judging whether the particle pattern formed in the reaction vessel is agglutinated or not in accordance with the comparison result.

10. An automatic particle pattern judging method according to claim 9, wherein:

said parameters comprise an area of said particle pattern formed in the bottom surface of the reaction vessel.

11. An automatic particle pattern judging method according to claim 9, wherein:

said parameter comprises the ratio between the light intensity of a center portion of the reaction vessel and that of a peripheral portion of the reaction vessel.

* * * * *